US011333660B2

(12) United States Patent
Scherr et al.

(10) Patent No.: US 11,333,660 B2
(45) Date of Patent: May 17, 2022

(54) ANALYTICAL PROCESS FOR PREDICTING THE THERAPEUTIC EFFECT OF BH3 MIMETICS

(71) Applicant: MEDIZINISCHE HOCHSCHULE HANNOVER, Hannover (DE)

(72) Inventors: Michaela Scherr, Hemmingen (DE); Matthias Eder, Burgdorf (DE)

(73) Assignee: Medizinische Hochschule Hannover, Hannover (DE)

( * ) Notice: Subject to any disclaimer, the term of this patent is extended or adjusted under 35 U.S.C. 154(b) by 205 days.

(21) Appl. No.: 16/500,307

(22) PCT Filed: Apr. 3, 2018

(86) PCT No.: PCT/EP2018/058509
§ 371 (c)(1),
(2) Date: Oct. 2, 2019

(87) PCT Pub. No.: WO2018/185112
PCT Pub. Date: Oct. 11, 2018

(65) Prior Publication Data
US 2021/0116439 A1    Apr. 22, 2021

(30) Foreign Application Priority Data
Apr. 4, 2017   (EP) .................................... 17164871

(51) Int. Cl.
*C12Q 1/00*     (2006.01)
*G01N 33/50*    (2006.01)

(52) U.S. Cl.
CPC ............................. *G01N 33/5011* (2013.01)

(58) Field of Classification Search
CPC ................................................ G01N 33/5011
See application file for complete search history.

(56) References Cited

U.S. PATENT DOCUMENTS

| 2013/0071323 A1 | 3/2013 | Gallatin et al. |
| 2013/0172266 A1 | 7/2013 | Kelley et al. |

FOREIGN PATENT DOCUMENTS

| WO | 20070146968 A2 | 12/2007 |
| WO | 20120071562 A2 | 5/2012 |
| WO | 20140047342 A1 | 3/2014 |
| WO | 20140059158 A1 | 4/2014 |
| WO | 20160115105 A1 | 7/2016 |

OTHER PUBLICATIONS

Zunino SJ et al. "Berry Fruit Extracts Inhibit Growth and Induce Apoptosis of High-Risk Acute Lymphoblastic Leukemia Cells in Vitro," Journal of Functional Foods, vol. 2 , pp. 187-195, 2010.
Aggarwal et al. "Murine Leukemia P388 Vinorelbine-resistant Cell Lines are Sensitive to Vinflunine," Invest New Drugs, pp. 319-330, 2008.
Lapalombella et al. "Tetraspanin CD37 Directly Mediates Transduction of Survival and Apoptotic Signals" Cell Press, pp. 694-708, 2012.
Zunino et al. "Parthenolide Induces Significant Apoptosis and Production of Reactive Oxygen Species in High-risk Pre-B Leukemia Cells" Cancer Letters 254, pp. 119-127, 2007.
Hussain et al. "Flavopiridol Causes Eady Mitochondrial Damage in Chronic Lymphocytic Leukemia Cells with Impaired Oxygen Consumption and Mobilization of Intracellular Calcium" Blood Journal, vol. 111, 3190-3199, 2008.
Scherr et al. "Differential Expression of miR-17~92 Identifies BCL2 as a Therapeutic Target in BCR-ABL-postitive B-lineage acute Lymphoblastic Leukemia" Leukemia, vol. 28, 554-565, 2014.
Billard, "BH3 Mimetics: Status of the Field and New Developments" Molecular Cancer Therapeutics, 1691-1700, 2013.
Crowley et al, "Measuring Mitochondrial Transmembrane Potential by TMRE Staining" Cold Spring Harbor Protocols, 1092-1096, 2016.
Chipuk et al, "Mitochondrial Outer Membrane Permeabilization during Apoptosis: the Innocent Bystander Scenario" Cell Death and Differentiation, vol. 13, 1396-1402, 2006.
Davids et al, "Targeting the B-Cell Lymphoma-Leukemia 2 Family" Journal of Clinical Oncology, vol. 30, 3127-3135, 2012.
Marmoy, Valerie, "International Search Report",Application No. PCT/EP2018/058509, dated Jun. 4, 2018.
Written Opinion of the International Searching Authority on the corresponding International Patent Application No. PCT/EP2018/058509, dated Oct. 8, 2019.
Lin, V., et al, "BH3 Mimetics for the Treatment of B-Cell Malignancies—Insights and Lessons from the Clinic", Cancers, Nov. 12, 2020, pp. 1-24, vol. 12, No. 3353.
Kale, J., et al., "Phosphorylation switches Bax from promoting to inhibiting apoptosis thereby increasing drug resistance" EMBO Reports, Jul. 9, 2018, pp. 1-21, vol. 19.

*Primary Examiner* — Albert M Navarro
(74) *Attorney, Agent, or Firm* — Greer, Burns & Crain, Ltd.; Steven P. Fallon

(57) ABSTRACT

The present invention relates to an analytical in vitro process for predicting the therapeutic effectiveness of at least one pharmaceutical compound in the treatment of leukemia and/or lymphoma, the process analysing the transmembrane potential of mitochondria in cells isolated from a patient by quantification of fluorescence emitted from a dye indicating induction of apoptosis.

16 Claims, 6 Drawing Sheets

ANALYTICAL PROCESS FOR PREDICTING THE THERAPEUTIC EFFECT OF BH3 MIMETICS

Figure 1A:
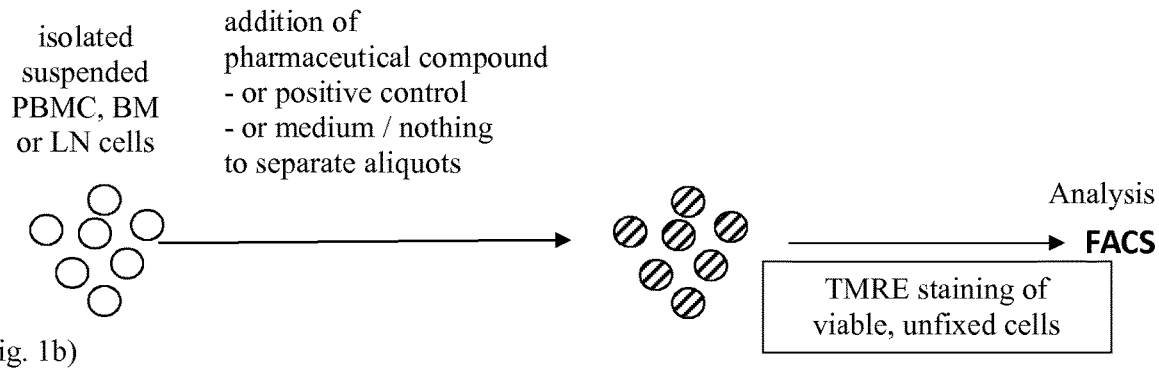

The present invention relates to an analytical process for predicting the therapeutic effectiveness of a pharmaceutical compound, which preferably is a BH3 mimetic, in the treatment of leukemia, including chronic lymphatic leukemia (CLL), preferably in acute myeloic leukemia (AML) or in acute lymphoblastic leukemia (ALL) as well as advanced chronic myeloid leukemia (CML) or lymphoma, including diffuse large B-cell lymphoma (DLBCL), Burkitt-lymphma, follicular lymphoma, mantle cell lymphoma, splenic marginal zone lymphoma, lymphoblasmocytic lymphoma, nodal marginal zone B-cell lymphoma, mediastinal large B-cell lymphoma, plasma cell myeloma, angioimmunoblastic T-cell lymphoma, anaplastic large cell lymphoma, T-cell prolymphocytic leukemia, T-cell LGL leukaemia, aggressive NK cell leukaemia, adult T-cell leukaemia/lymphoma, extranodal NK/T cell lymphoma (nasal type), enteropathy-type T-cell lymphoma, hepatosplenic T-cell lymphoma, subcutaneous panniculitis-like T-cell lymphoma, Mycosis fungoides, Sezary syndrome, primary cutaneous anaplastic large cell lymphoma and peripheral T-cell lymphoma, unspecified. The analytical process is an in vitro process analysing peripheral blood mononuclear cells (PBMC), bone marrow (BM) cells or cells from lymph nodes (LN) from patients who are diagnosed to have or are suspected of having leukemia or lymphoma in order to determine the effectiveness of a pharmaceutic compound. The analytical process has the advantage of directly measuring the compounds cytotoxicity in viable primary tumour cells and of giving an analytical result within a short time period, e.g. in less than 4 h, preferably in less than 2 h, more preferably in less than 1 h. As patients individually respond to administered pharmaceutic compounds, especially to BH3 mimetics, predicting the response prior to therapeutic administration of the pharmaceutical is desirable. Especially in the case of acute forms of leukemia and high-grade lymphoma it is desirable to predict the response of the patient to a certain pharmaceutical within a short time.

STATE OF ART

WO2016/115105 A1 describes an indirect method for determining the cancer treatment for a patient by analysing the BH3 profile of cancer cells (apoptotic priming). Cells that were e.g. obtained from a patient under treatment were permeabilized in the presence of added BH3 peptide, e.g. BIM, NOXA, Puma, HRK, BAD or BID in the case of leukocytes from AML or MDS leukemia patients, and Digitonin for permeabilization and oligomycin, followed by staining with JC-1 dye and FACS analysis.

WO 2014/047342 A1 describes a method for predicting the sensitivity of a cell to a therapeutic agent by contacting the cell, which is permeabilized, with a pro-apoptotic BH3 domain peptide and then measuring the mitochondrial outer membrane permeabilization (MOMP). For measuring MOMP, the dye JC-1, dihydrorhodamine 123, tetramethylrhodamine methyl ester or tetramethylrhodamine ethyl ester (TMRE) can be used for later detection by FACS.

These publications relating to measurement of MOMP consistently use perforated cells and pro-apoptotic BH3 domain peptides.

Crowley et al., Cold Spring Harb Protoc 2016 (doi10.1101/pdb.prot087361) describe measurement of the transmembrane potential of mitochondria by quantification of TMRE fluorescence in flow cytometry, e.g. to indicate triggering apoptosis in cells by a cytotoxic drug.

Scherr et al., Leukemia 225-565, 28 (2014) found that overexpression of the oncomir miR-17~19b in BCR-ABL-positive acute lymphoblastic leukemia (ALL) triggered apoptosis in a BCR-ABL-dependent manner and conclude that Bcl2 is a direct target of the miRNA cluster miR-17~19b.

Chipuk et al., Cell Death and Differentiation 1396-1402, 13 (2006) review the influence of the cytosol on MOMP, which is considered the point of no return of the apoptotic cascade that is governed by proteins of the BCL-2 family of proapoptotic proteins.

Davids and Letai, Journal of Clinical Oncology 3127-3135 (2012) discuss that certain small molecule BH3 mimetics which bind to the mitochondrial BCL-2 protein displace proapoptotic proteins from BCL-2, resulting in apoptosis. For prediction, it is quoted that the balance of cellular proteins NOXA/MCL-1 may determine the sensitivity to the BH3 mimetic ABT-737, and that it was found that the clinical response of CLL patients to the BH3 mimetic ABT-263 correlates with low MCL-1 expression, high BIM-MCL-1 ratio, or high BIM-BCL-2 ratio.

Billard, Mol Cancer Ther 12 (9), 1691-1700 (2013) describe BH3 mimetics as a group of small molecules, non-peptide or derived from BH3 proteins, that mimic the BH3-only proteins by inserting their BH3-like domain into the hydrophobic groove of the pro-survival BCL-2 proteins, inhibiting their functional activity and thus inducing apoptosis. Exemplary BH3 mimetics include ABT-199, available as a medicament named Venetoclax that has recently been approved for therapy of 17p-deleted or refractory chronic lymphocytic leukemia (CLL).

Hussain et al., Blood 111 (6), 3190-3199 (2008) focus on determining the mechanisms of Flavopiridol in order to predict which patients are at increased risk for acute tumour lysis syndrome with Flavopiridol treatment and describe that mitochondrial membrane depolarization was detected in blood cells obtained from a CLL patient at 6 h after the cells were contacted in vitro with Flavopiridol. For FACS measurements, the dye JC-1 was used and cells were regarded as intact when falling into a gate that was pre-determined for aggregated JC-1 (intact mitochondria) in untreated cells.

It is known that leukemic blast cells from the peripheral blood, bone marrow or lymph nodes in vitro have a very limited life span, in particular ALL-blasts e.g. after isolation. For predicting the effectiveness of pharmaceuticals on apoptosis, prior art methods that analyse PBMC in leukemia patients use fixed, perforated cells and determine cellular regulatory proteins or add cellular regulatory proteins for their effect on mitochondrial outer membrane permeabilization (MOMP) as an indirect means to determine "apoptotic priming". Both WO2016/115105 A1 and WO 2014/047342 A1 quantify the state of mitochondrial or apoptotic priming as determined by induction of MOMP by BH3 peptides added to permeabilized cells. This analyses an indirect surrogate marker for cytotoxicity of a compound.

OBJECT OF THE INVENTION

The object of the invention is the provision of an analytical in vitro process for direct determination of the effectiveness of a compound to induce mitochondrial outer membrane permeabilization (MOMP) and thereby apoptosis in leukemic cells from the peripheral blood, bone marrow or lymph nodes of leukemia or of lymphoma patients, especially in chronic lymphatic leukemia (CLL), preferably in acute myeloic leukemia (AML) or in acute lymphatic leukemia (ALL) as well as advanced chronic myeloid leukemia (CML) or all types of lymphoma. The desired in vitro process shall be faster than a prior art process and is unique in predicting effectiveness of BH3 mimetics.

DESCRIPTION OF THE INVENTION

The invention achieves the object by the features of the claims, especially by an analytical in vitro process for predicting the therapeutic effectiveness of at least one pharmaceutical compound in the treatment of leukemia and/or lymphoma, the process comprising or consisting of the steps of isolating peripheral blood mononuclear cells from a blood sample (PBMC) or bone marrow cells (BM) or cells from a lymph node (LN), transferring the isolated PBMC, BM or LN mononuclear cells into a medium sustaining viability of the PBMC, BM or LN cells, adding the pharmaceutical compound or a combination of at least two of such compounds to at least one concentration to the medium containing the isolated PBMC, BM or LN mononuclear cells, wherein each compound, each concentration and each combination of compounds is added to a separate aliquot of the medium containing the isolated PBMC, BM or LN mononuclear cells, incubating the PBMC, BM or LN mononuclear cells in the medium with the added pharmaceutical compound under cell culture conditions, preferably for a short period of time, adding a fluorescent dye labelling active mitochondria in living cells to the medium containing the PBMC, BM or LN mononuclear cells and the pharmaceutical compound, and measuring for each of the separate aliquots on the PBMC, BM or LN mononuclear cells the transmembrane potential of mitochondria by quantification of fluorescence emitted from the dye. In the process, the isolated cells are viable and are kept under cell culture conditions, e.g. without perforating the cells.

Preferably, the at least one pharmaceutical compound is a BH3 mimetic. More preferred, in the process at least two, preferably at least three different pharmaceutical compounds, which preferably are BH3 mimetics, are added in each case to separate aliquots of the medium containing the isolated PBMC, BM or LN cells, which separate aliquots preferably are processed in parallel.

A BH3 mimetic is a pharmaceutical compound that mimics the binding of the BH3 domain of Bcl-2 (B-cell lymphoma 2) family proteins. Pro-apoptotic BH3 only proteins such as BIM bind to the BH3 binding groove in pro-survival proteins such as Bcl-2, Bcl-XL or Mcl-1. Accordingly, BH3 mimetics bind to and block the BH3 binding groove within pro-survival proteins thereby facilitating induction of mitochondrial apoptosis.

The process in which at least one, preferably at least two or at least three different pharmaceutical compounds are processed, by measuring the transmembrane potential of mitochondria in the cells allows to determine the pharmaceutical compound which has the best efficacy for the individual patient from whom the sample originates. The process allows to identify from the pharmaceutical compounds analysed the individual pharmaceutical compound which is most effective for the individual sample, and/or to monitor the efficacy of each compound against the cells, e.g. during the course of the treatment, e.g. using a sample originating at a later point in time from the same patient. In this embodiment of the process, subsequent to the process being carried out on an initial sample, the process is additionally carried out on at least one sample, which originates from the same patient at a later point in time, wherein to an aliquot the same at least one pharmaceutical compound is added that was added to the initial sample, for monitoring the efficacy of the at least one pharmaceutical compound on the sample originating from the same patient at a later point in time. This embodiment is e.g. for monitoring efficacy of the same pharmaceutical compound on an initial sample and on a sample taken at a later point in time from the same patient, preferably for detecting development of resistance of the tumour cells against the same compound during the course of the treatment.

During the process, the viability of the isolated PBMC, BM or LN mononuclear cells is maintained, and especially the medium containing the PBMC, BM or LN mononuclear cells and the incubation conditions sustain viability of the PBMC, BM or LN mononuclear cells, except for the added pharmaceutical compound and except for a protonophor that is added optionally to an aliquot of PBMC, BM or LN mononuclear cells in the medium and under otherwise identical conditions as a positive control for an effective compound added.

The analytical process can be carried out within a short period of time so that the short in vitro survival time of leukemic cells is not hampering the analysis. Further, the analytical process avoids the analysis of cellular proteins or of genetic aberrations. Therefore, the analytical process is useable for direct prediction of the clinical response of an individual patient to a specific BH3 mimetic without need for analysis of surrogate markers such as e.g. molecular analyses of tumour markers or cytogenetics and molecular genetics as used in e.g. certain solid tumours.

The fluorescent dye can e.g. be dye JC-1, dihydrorhodamine 123, tetramethylrhodamine methyl ester, preferably tetramethylrhodamine ethyl ester (TMRE), e.g. added to a final concentration of 50 nM. The protonophor can e.g. be carbonyl cyanide-4-(trifluoro-methoxy)phenylhydrazone (FCCP), e.g. added to a final concentration of 5 µM. The assay preferably uses TMRE since it measures the general health of mitochondria and allows parallel staining of the cells with dye-labelled antibodies. These dye-labelled antibodies may include anti-CD19 for B-lymphoid tumour cells, anti-CD3, anti-CD4 or anti-CD8 for T-lymphoid tumour cells, and anti-CD34, anti-CD33, anti-CD45 (low expression) or anti-CD117 antibodies for myeloid tumour cells or neoplasms, respectively. Optionally, the process includes the step of analysing, preferably within the same FACS analysis, the signal of the fluorescent dye indicating MOMP, e.g. of TMRE, both for the tumour cells and for non-tumour cells. Therein, the analysis of the signal of the fluorescent dye indicating MOMP separately for the tumour cells allows to monitor the efficacy of the pharmaceutical compound against the tumour cells, and analysing the signal of the fluorescent dye indicating MOMP for the non-tumour cells allows to monitor the impact of the pharmaceutical compound on the non-tumour cells, which indicates unwanted side-effects. Tumour cells are e.g. lymphoma and/or leukemia cells, e.g. selected from the group consisting of CD19+ cells, CD3+ cells, CD4+ cells, CD8+ cells, CD34+ cells, CD33+ cells, CD45+ low expression cells, or CD117+ cells. Non-tumour cells are e.g. negative for CD19, negative for CD3, negative for CD4, negative for CD8, negative for CD34, negative for CD33, negative for CD117, and/or CD45+ high expressing cells.

Preferably, the fluorescent dye labelling active mitochondria in living cells is TMRE, and, preferably concurrent to measuring the transmembrane potential of mitochondria by quantification of fluorescence emitted from TMRE, the process includes the step of labelling cells using one of the aforementioned dye-labelled antibodies, for example for determining e.g. CD19+ cells, e.g. by adding a fluorescently labelled anti-CD19 antibody. The fluorescence label of the dye-labelled antibody, e.g. of an anti-CD19 antibody, can emit green fluorescence. This is relevant for heterogeneous cell samples which contain e.g. B-lymphoid tumour cells (CD19+) and normal e.g. T-lymphocytes or monocytes (CD19−) to differentially analyse the response to a pharmaceutical compound, which preferably is a BH3 mimetic, in tumour and normal cells as a surrogate for the therapeutic window of the compound, e.g. BH3 mimetic, tested.

Generally preferred, the process includes all PBMC, BM or LN cells of the sample, e.g. the process does not include a step of isolating e.g. B-lymphoid CD19+ cells, and measuring on the PBMC, BM or LN cells the transmembrane potential by quantification of fluorescence is by fluorescence assisted cell sorting (FACS), wherein measurement of forward scatter and of side scatter is used to set the measuring parameters, also termed gating, to determine live and dead cells for each sample tested.

Optionally, measuring on the PBMC, BM or LN cells the transmembrane potential by quantification of fluorescence is by FACS, wherein preferably the cells are also immunologically stained for CD19, e.g. adding a fluorescence labelled anti-CD19 antibody, and the measurement determines the proportion of CD19+ cells which show MOMP, e.g. as indicated by a reduced fluorescence by TMRE.

Preferably, the process for quantifying fluorescence from the dye for measuring the transmembrane potential of mitochondria is set to determine the gating for live cells from forward scatter and side scatter, and applying the gating for live cells to identify live tumour cells using immunological staining, e.g. CD19+ cells using immunological staining for CD19, and to measure for live tumour cells, e.g. CD19+ (CD19 positive) cells the proportion of cells showing MOMP by quantifying the fluorescence from the dye for measuring the transmembrane potential of mitochondria.

Optionally additionally, the fluorescence of the dye for measuring transmembrane potential of mitochondria is determined for CD19− (CD19 negative) cells, e.g. in order to determine the proportion of live non-tumour cells, e.g. on CD19− cells, that undergo MOMP caused by the pharmaceutical compound, e.g. for assessment of unwanted side effects of the pharmaceutical compound. This allows quantification of the therapeutic window and adverse effects of the pharmaceutical compound on normal cells, e.g. non-tumour cells, in one FACS analysis. Generally, the process includes at least one aliquot of the mononuclear cells treated in parallel with no pharmaceutical compound added as a negative control, and preferably at least one aliquot of the mononuclear cells treated in parallel with a compound known to induce MOMP, preferably known to induce MOMP independent from BH3-mimetics and within a short time as a positive control, e.g. FCCP.

Preferably, in the process one preparation of isolated PBMC, BM or LN mononuclear cells suspended in the medium is distributed into separate aliquots which are processed in parallel. The at least one pharmaceutical compound, which can be a combination of at least two compounds, is added to at least two of these aliquots, preferably added to at least at two different final concentrations, at least one other aliquot is processed without addition of an active compound as a negative control, e.g. without addition of a further compound or with addition of an inactive composition like medium or physiological saline, and at least one other aliquot is processed by adding a compound known to disrupt the mitochondrial outer membrane as a positive control, with subsequent incubation of the aliquots under the same cell culture conditions, addition of the fluorescent dye that labels active mitochondria in the isolated PBMC, BM or LN mononuclear cells, optionally with an additional incubation under cell culture conditions, followed by measuring fluorescence emitted from the dye for each aliquot.

Preferably, in the process at least one or more pharmaceutical compounds, which preferably are BH3 mimetics, are processed in parallel in separate aliquots of the isolated PBMC, BM or LN mononuclear cells suspended in the medium, in order to determine, which of these at least two different pharmaceutical compounds, e.g. BH3 mimetics, has the more intense efficacy against the leukemia or lymphoma cells.

It was found that during treatment, certain leukemia or lymphoma patients at a later point in time become resistant against treatment with an initially effective BH3 mimetic, and that the analytical process allows to select another BH3 mimetic according to its efficacy, which BH3 mimetic then is for use in the treatment of the leukemia or lymphoma showing resistance against the initially used BH3 mimetic.

More preferably, subsequent to the process being carried out on an initial sample, the process is additionally carried out on at least one same sample, which originates from the same patient at a later point in time, e.g. for monitoring the efficacy of at least two different pharmaceutical compounds, which preferably are BH3 mimetics, and the determination of the pharmaceutical compound which has the more intense efficacy against the leukemia or lymphoma cells of the sample originating from the same patient at a later point in time. In this embodiment, the process allows to monitor the efficacy of the BH3 mimetics and to select a pharmaceutical compound, which preferably is a BH3 mimetic, having a more intense efficacy also e.g. in samples originating from a patient who shows a decline in the efficacy of the pharmaceutical compound, e.g. BH3 mimetic, used for treatment, e.g. in samples originating from patients showing resistance against treatment with a certain compound, preferably a BH3 mimetic, e.g. samples from refractory patients. This allows monitoring and selection of effective pharmaceutical compounds, especially of BH3 mimetics, during the course of therapy for individual patients.

Combinations of compounds such as two BH3 mimetics with different binding profiles can be tested simultaneously by addition of the two drugs to a single aliquot. The measurement results for the different aliquots, each separate aliquot containing one BH3 mimetic, or each separate aliquot containing a combination of at least two pharmaceutical compounds, e.g. at least two BH3 mimetics, can be evaluated by comparing the results obtained for the aliquots with an added pharmaceutical compound with the results of the negative control and of the positive control. Measurement results for the aliquots with one added pharmaceutical compound, or with at least two pharmaceutical compounds, which results are between the result measured for the negative control and the result for the positive control indicate apoptotic effectiveness of the pharmaceutical compound for the PBMC, BM or LN mononuclear cells, whereas results for the aliquots with one added pharmaceutical compound, or respectively with at least two added pharmaceutical compounds, in the range of the negative control indicate that the pharmaceutical compound does not induce apoptosis in the PBMC, BM or LN mononuclear cells of the specific patient, e.g. that the PBMC are resistant against the pharmaceutical compound or the combination of compounds tested.

The medium is composed to sustain viability of the isolated PBMC, BM or LN mononuclear cells preferably is a cell culture medium. The cell culture conditions applied during incubation of the PBMC, BM or LN mononuclear cells in the medium can e.g. be 37° C., 5% $CO_2$ in air.

Preferably, the PBMC, BM or LN mononuclear cells in the medium are in suspension during the process. The process does not contain any steps for fixation nor for permeabilization of PBMC, BM or LN cells so induction of MOMP and apoptosis can directly be determined in viable cells. As a result of sustaining viability of the PBMC isolated from a blood sample, isolated BM or LN mononuclear cells, the process directly determines the effectiveness of an added pharmaceutical compound onto PBMC, BM or LN mononuclear cells by measuring the resultant transmembrane potential of mitochondria. Accordingly, the process yields a direct measurement result on the apoptotic effect of the compound(s) added. Therein, the decrease of transmembrane potential of mitochondria due to mitochondrial outer membrane permeabilization (MOMP), is measured as an indicator for and preceding apoptosis. Therefore the process does not include any steps of analysing proteins, e.g. no steps for analysing for presence or absence of mutant proteins or of pro-apoptotic proteins or anti-apoptotic proteins or of relative expression levels of such proteins, and no addition of further compounds, e.g. no addition of pro-apoptotic proteins or peptides or of anti-apoptotic proteins or peptides.

The process has the advantage of a short duration, so that the desired result of the effectiveness of the pharmaceutical compound added to the isolated PBMC, BM or LN mononuclear cells is obtained within a short period of time, e.g. in under 4 h, preferably in under 3 h, more preferably in under 2 h or in under 1 h, starting from isolated PBMC, BM or LN mononuclear cells and does not interfere with the short survival time of leukemic blast cells in vitro. This short duration of the process is advantageous, especially for acute forms of leukemia, as it allows the administration of the pharmaceutical compound to the patient after the short duration, without a longer delay. The blood, BM or LN sample originates from a patient who was diagnosed as or is suspected of having leukemia, especially chronic lymphatic leukemia (CLL), preferably acute myeloic leukemia (AML) or acute lymphatic leukemia (ALL) and advanced chronic myeloid leukemia (CML) or all kind of lymphoma. The blood, BM or LN sample originating from a patient generally can be drawn prior to the analytical process.

In one embodiment, the analytical process is performed on a blood, BM or LN sample originating from a patient who is suspected of having leukemia or lymphoma, especially an acute form of leukemia, prior to the end of the diagnostic procedure, especially prior to the end of a diagnostic procedure which includes the determination of genetic, chromosomal or molecular aberrations. For the analytical process of the invention, the precise diagnosis need not be known, because the process directly measures the effectiveness of a pharmaceutical compound onto viable tumour cells from peripheral blood, bone marrow or lymph nodes. In the alternative, the sample can originate from a patient diagnosed as a relapse of leukemia or lymphoma.

It has been found that the analytical process determines the effectiveness of a pharmaceutical compound in a concentration-dependent manner, which is interpreted as an indication that the process only determines the effectiveness in respect of inducing apoptosis in isolated PBMC, BM or LN mononuclear cells without additional effects caused by a higher concentration of the pharmaceutical compound. Therefore, the analytical process can be done at concentrations of the pharmaceutical compound higher than the pharmacological concentrations adjusted in the patient. For example, the concentration of the pharmaceutical compound in the process can be higher by a factor of at least 2 or a factor of at least 5 or by a factor of at least 10, preferably higher by a factor of at least 100, more preferred higher by a factor of at least 1000 than the pharmacological concentrations adjusted in the patient. The pharmacological concentrations adjusted in the patient can e.g. be determined by the recommended dosage of the pharmaceutical compound. At higher concentrations of the pharmaceutical compound, the process can be performed in a shorter duration, e.g. in less than 1 h, e.g. within 40 min, preferably within 30 min, starting from the isolated PBMC, BM or LN cells, i.e. measured from the end of the isolation of the respective cells. Furthermore, the induction of MOMP in isolated leukemic PBMC, BM or LN mononuclear cells by the compound, which preferably is a BH3 mimetic, always precedes and leads to cellular apoptosis under physiologic conditions so MOMP induction can be used as a reliable predictor for cytotoxicity of the compound analysed.

The quantification of fluorescence preferably is by FACS, irradiating with a wavelength to excite fluorescence from the dye for detecting a change of fluorescence emitted due to changes of the mitochondrial outer membrane potential, e.g. a decrease of fluorescence of the dye due to decreasing mitochondrial outer membrane potential, indicating apoptosis, and preferably setting the gating for separate detection of cells.

Preferably, the pharmaceutical compound is a BH3 mimetic, e.g. selected from ABT-199 (i.e. Venetoclax), ABT-737, ABT-263, WEHI-539, BM-1074 (binding to BCL2 and BCL-XL) MCL-1 inhibitors such as AMG 176 or MIK 665 (S64315), or AT1 (Gossypol) or TW-37 (both binding to BCL2, BCL-XL and MCL1) or compounds targeting or binding to BCL2, BCL-XL, BCL-w, MCL-1 and/or Bfl-1 (A1) or combinations of at least two of these pharmaceutical compounds. Furthermore, the analytical process according to the invention is able to directly quantify the effects of compounds targeting or binding to the so-called sensitizer BH3-only proteins, especially targeting or binding to NOXA, PUMA, BAD, BIK, HRK, BMF.

PBMC, BM or LN mononuclear cells can be isolated from a blood, bone marrow or lymph node sample, respectively by density gradient centrifugation, e.g. using a polymer like Ficoll or Biocoll. The blood, bone marrow or lymph node sample can be a native blood, bone marrow or lymph node sample, optionally containing an anti-coagulation agent, e.g. EDTA, or a heparinized blood sample.

For isolation of PBMC or BM mononuclear cells, the blood or BM sample, preferably after dilution 1:2 in phosphate buffered saline (PBS) is layered onto 20 mL Ficoll in a centrifugation tube, e.g. a 50 mL tube, followed by centrifugation for 20 min at 2000 rpm. These steps can be carried out at room temperature. The upper layer is removed from the centrifuged tube and the mononuclear cell layer is aspirated and transferred into a clean tube and washed with addition of PBS, centrifugation for 10 min at 2500 rpm and removal of the supernatant. For lysis of erythrocytes, the pellet is resuspended in 0.83 wt.-% ammonium chloride in water and incubated for 15 min at 37° C., 5% $CO_2$ in air. PBMC are collected by centrifugation at 1300 rpm for 15 min, the supernatant is discarded and the pelleted PBMC are resuspended in PBS, centrifuged at 1300 rpm for 5 min for washing and resuspended in medium sustaining viable cells, e.g. in RPMI1640 cell culture medium, preferably supplemented with 10% fetal calf serum and 1% penicillin/streptomycin.

Figure 1B:
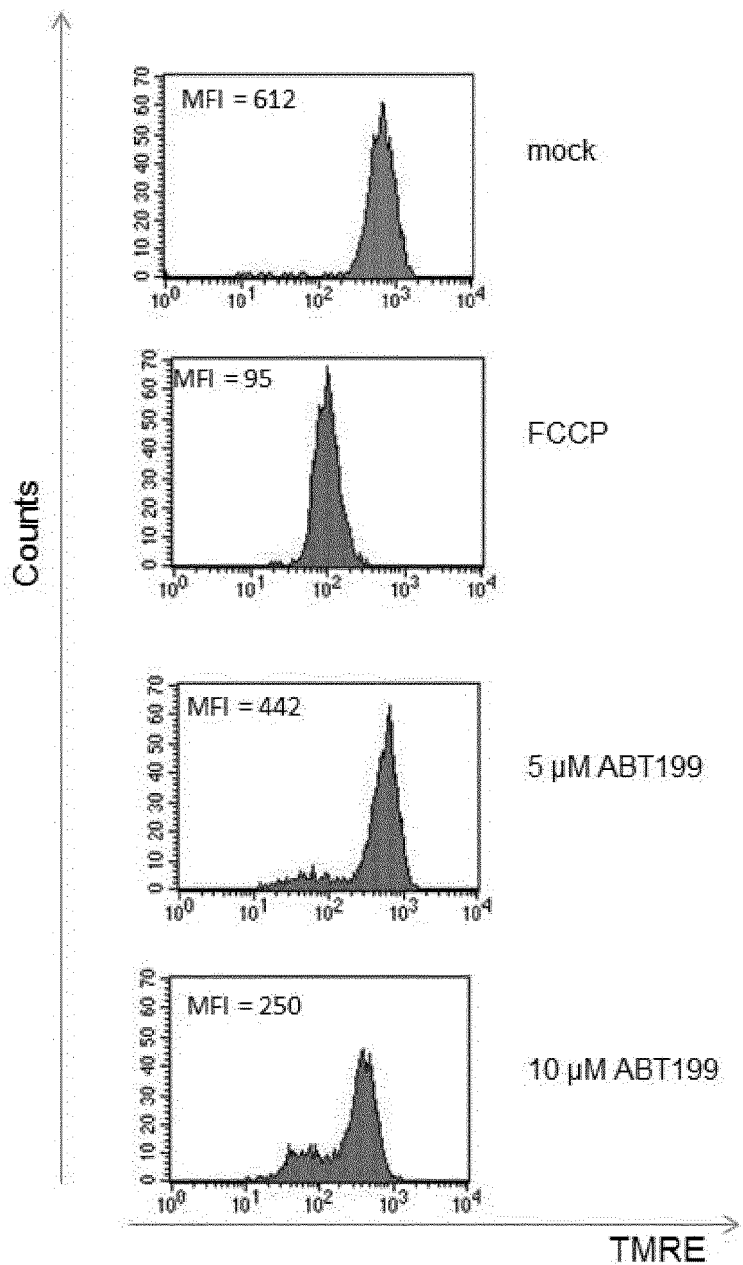
Figure 2:
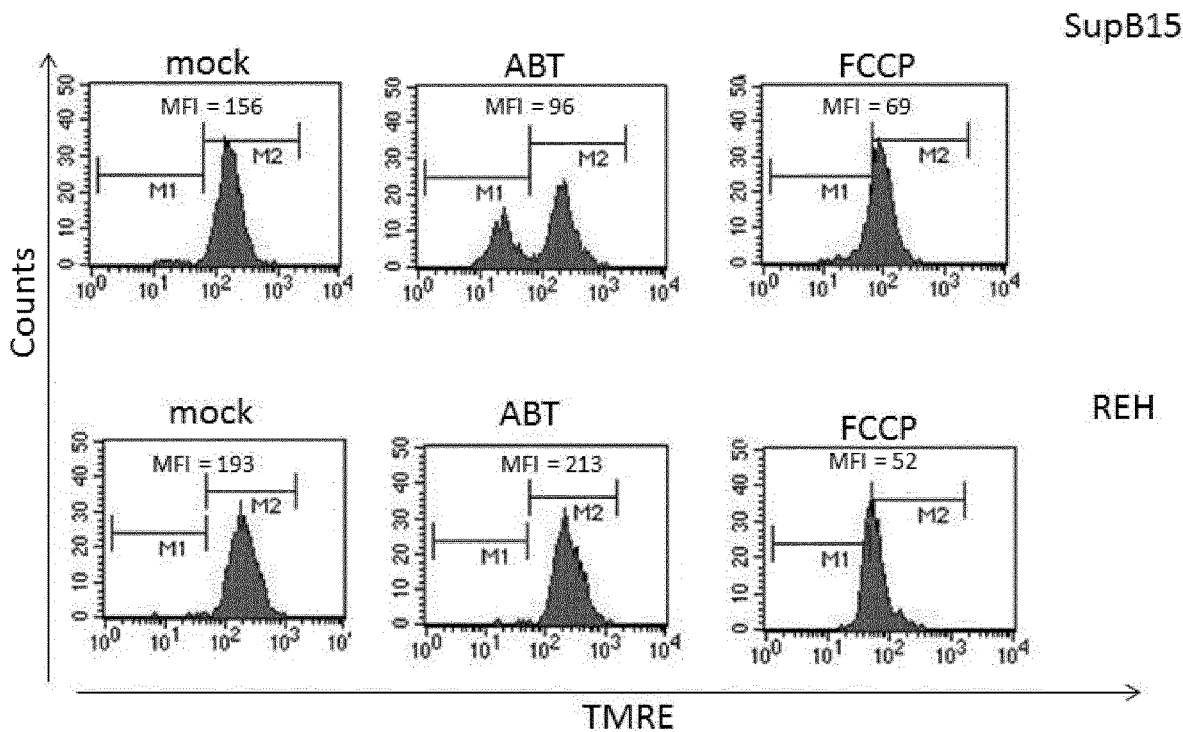
Figure 3:
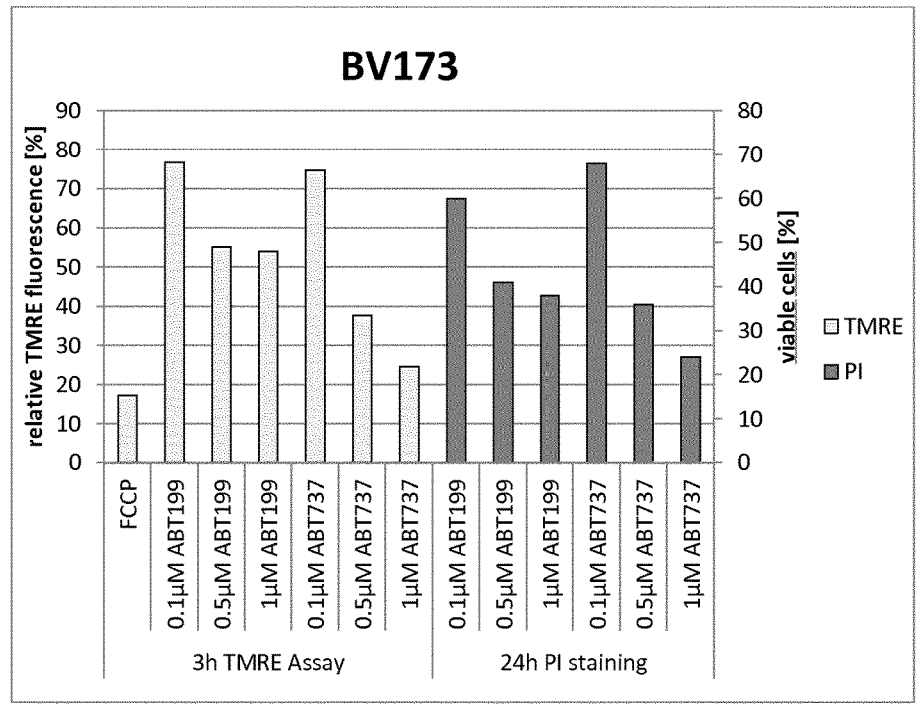
Figure 4:
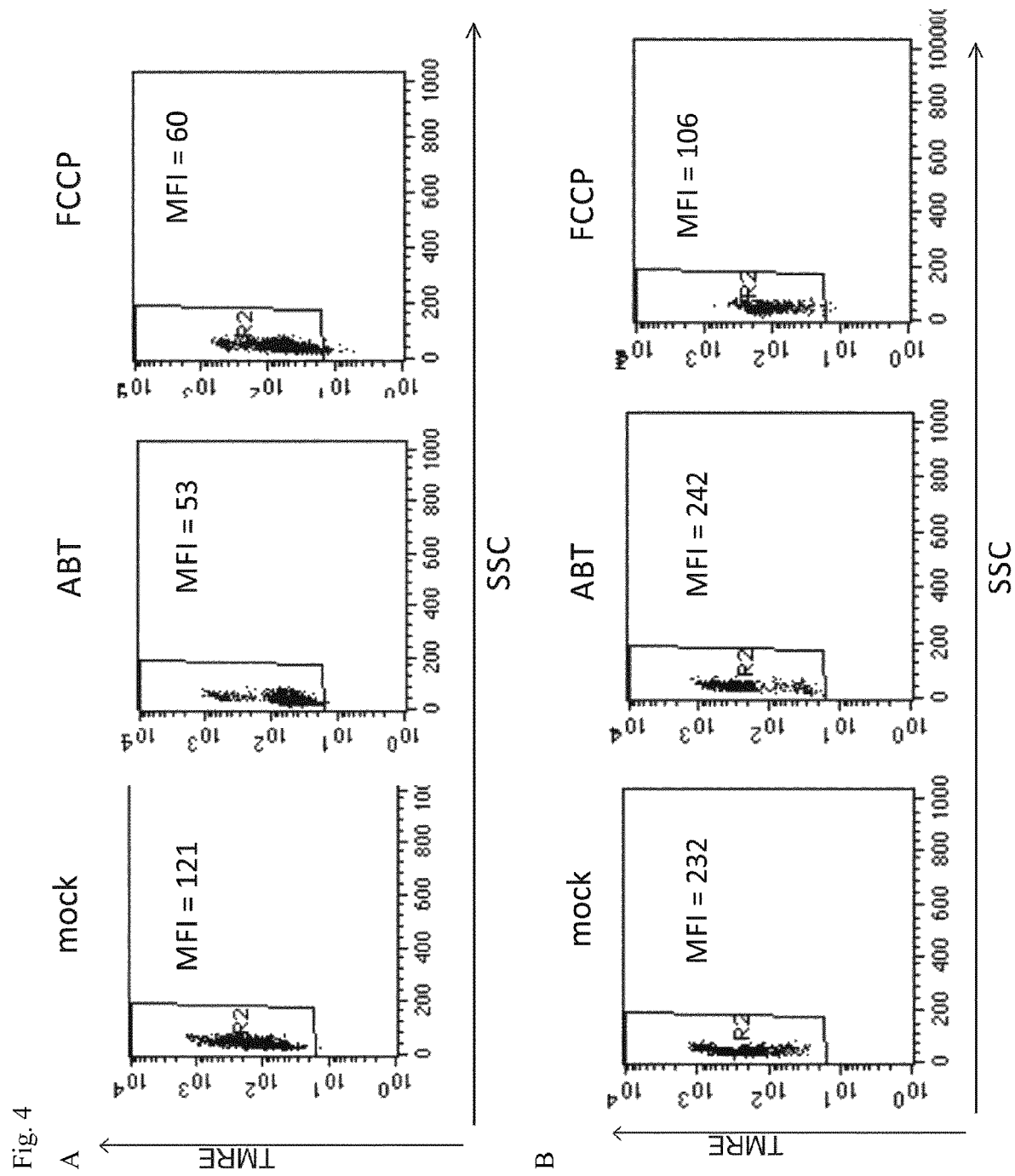
Figure 5:
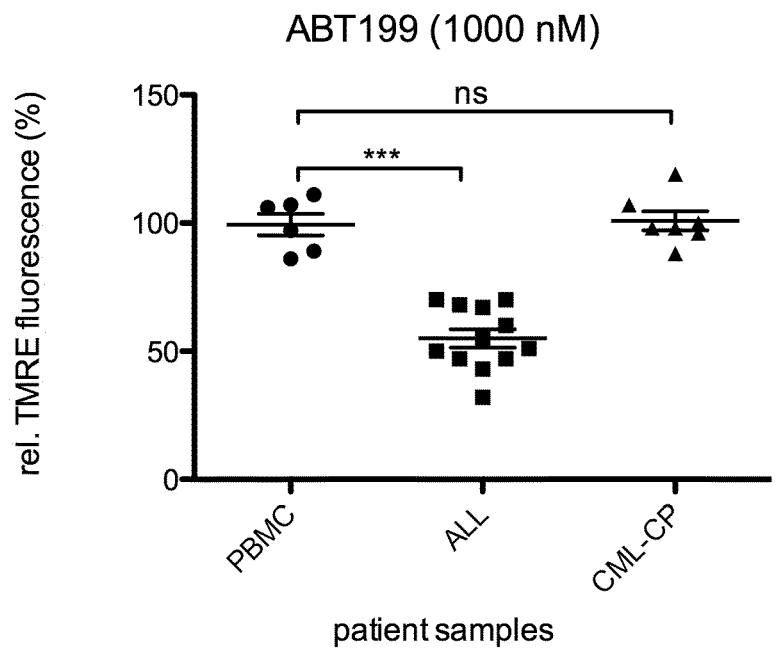
Figure 6:
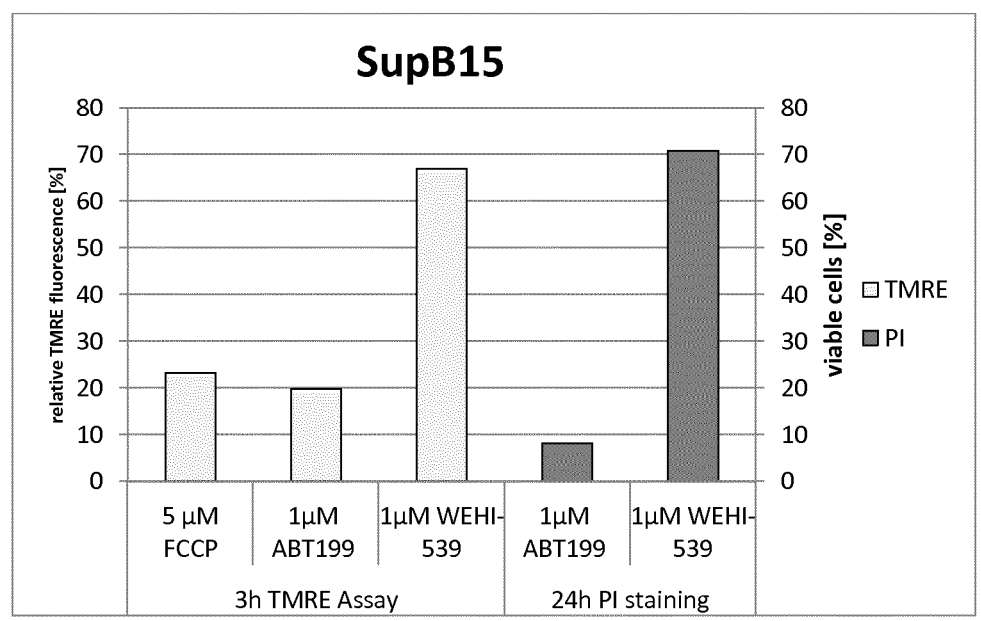
Figure 7:
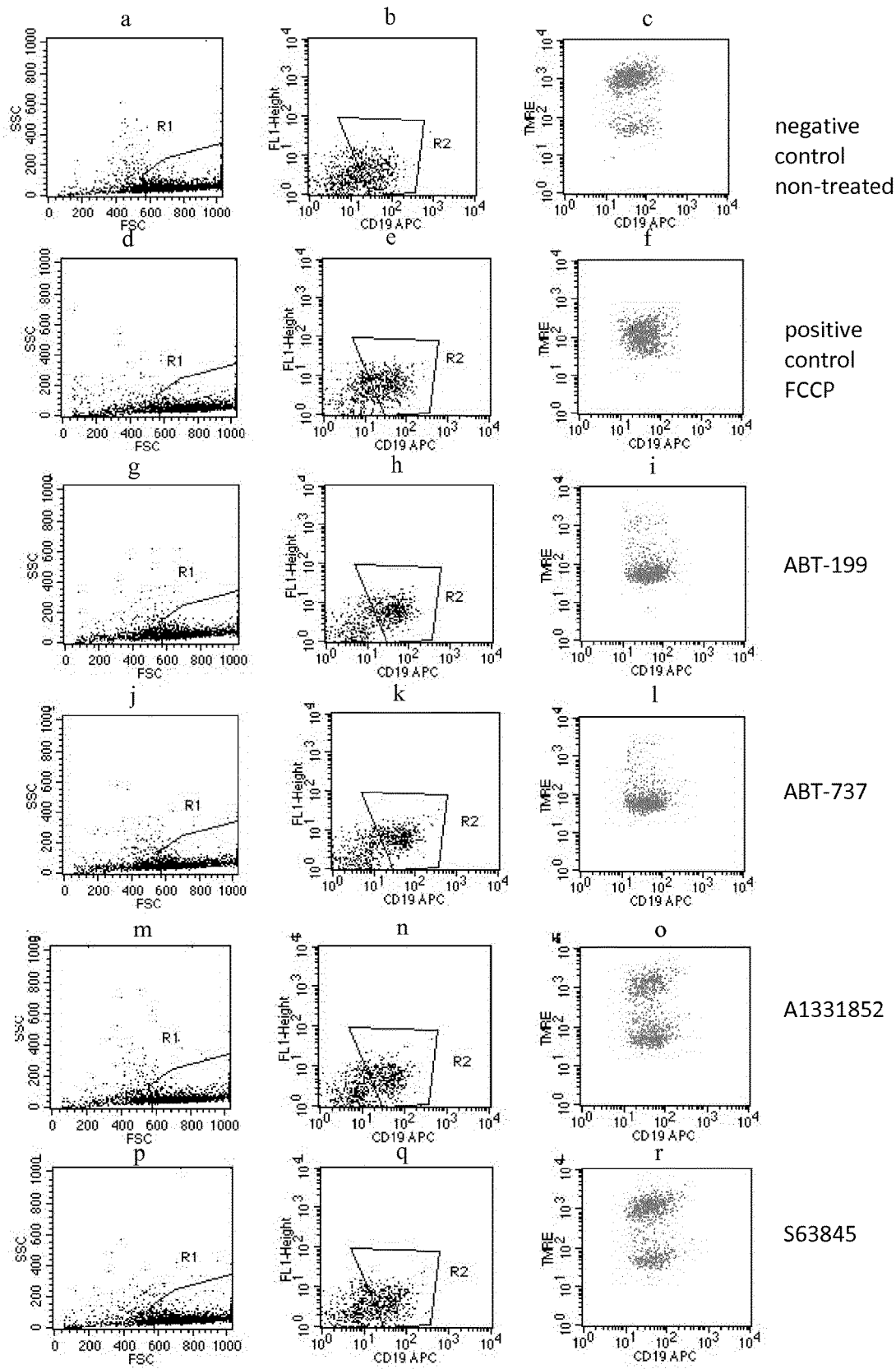
Figure 8:
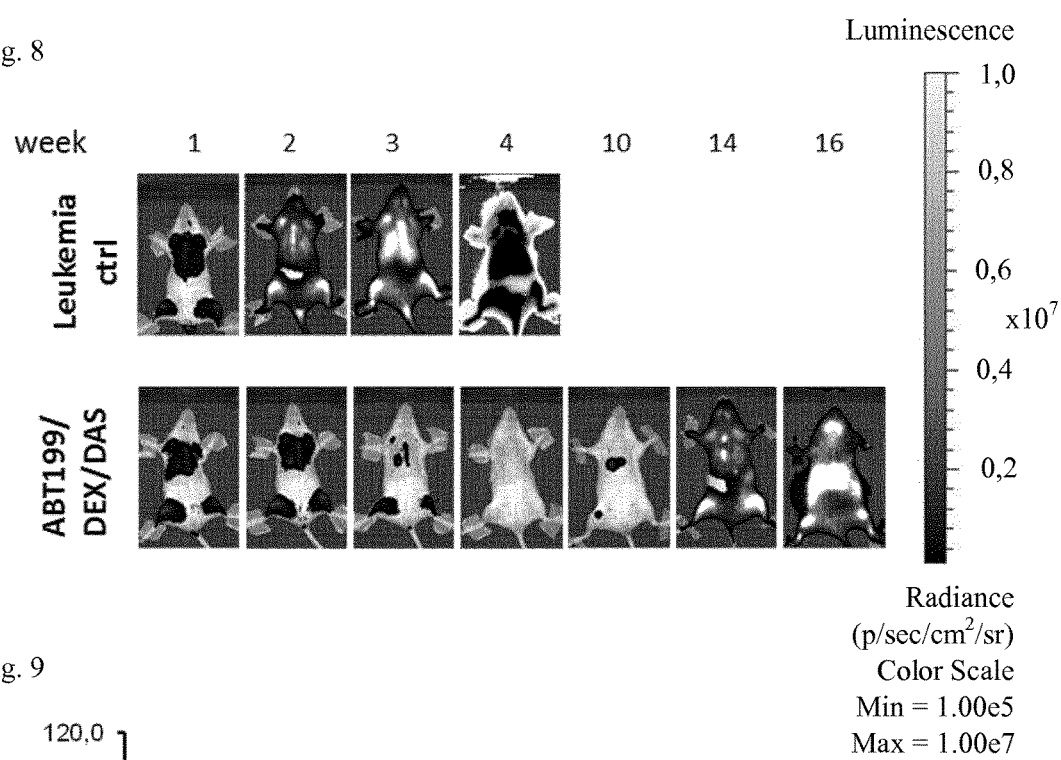
Figure 9:
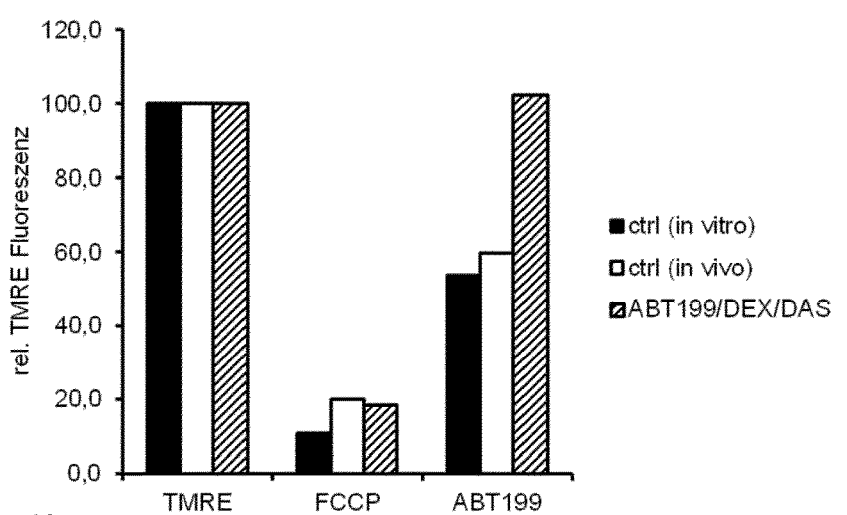
Figure 10:
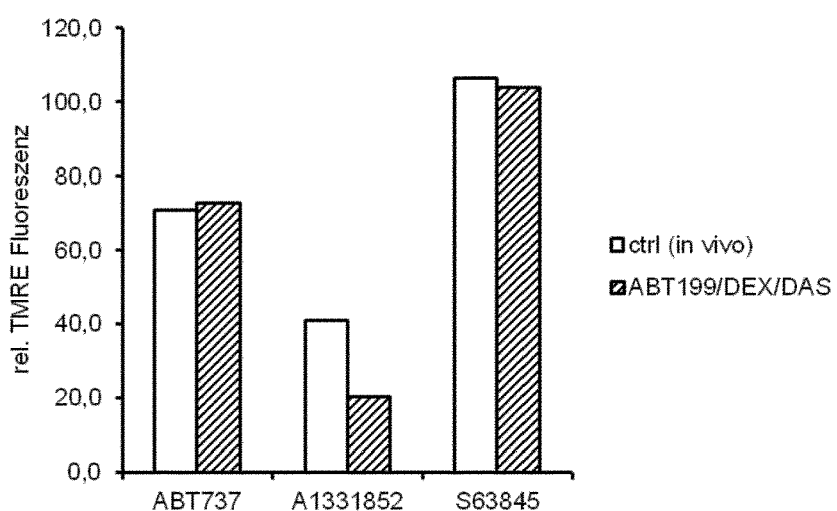

The invention is now described in greater detail by way of examples with reference to the figures, which show in FIG. 1 a) a schematic representation of the analytical process and b) FACS results, FIG. 2 FACS results measured by the analytical process for two cell lines SupB15 and REH, respectively, FIG. 3 a comparison between measurement results of the analytical process and propidium iodide staining as a comparison for a cell line (BV173), FIG. 4 FACS results measured by the analytical process for PBMC, in A for blood from a CLL patient, in B for a healthy donor, FIG. 5 results of the analytical process for PBMCs from healthy donors and different leukemic patients, FIG. 6 results of the analytical process for a very and a less effective BH3 mimetic in comparison to propidium iodide staining as a comparison for a cell line (SUPB15), FIG. 7 staining of CD19+ tumour cells and tumour-specific FACS measurement results for aliquots of PBMC originating from a patient sample treated with different BH3 mimetics, positive and negative control, FIG. 8 bioluminescence imaging pictures of leukemic mice under therapy, FIG. 9 a graph showing relative induction of MOMP in spleen cells isolated from experimental drug-resistant animals shown in FIG. 8, and in FIG. 10 a graph showing relative induction of MOMP in spleen cells isolated from experimental animals shown in FIG. 8 after in vitro addition of different pharmaceutical compounds.

For the FACS analyses described, gating of forward scatter (FSC) and side scatter (SSC) was generally set to measure only vital cells.

FIG. 1a) schematically shows the analytical process of the invention, in which preferably aliquots of a preparation of PBMC, BM or LN mononuclear cells that were isolated from a blood, bone marrow or lymph node sample are suspended in medium which sustains viability of the PBMC, BM or LN cells, and adding to separate aliquots a pharmaceutical compound at least to two different concentrations, a protonophor, e.g. FCCP as a positive control generating MOMP, and to another aliquot, nothing as a negative control serving as a background control for apoptosis.

Exemplary FACS measurements obtained by the analytical process of the invention for the different aliquots is shown in FIG. 1b), showing for the negative control (mock) essentially one peak and a mean fluorescence intensity (MFI) of 612, for the positive control (FCCP) essentially one peak to the left of the negative control peak (MFI 95), and for the aliquots with ABT-199 added as the pharmaceutical compound two peaks, at the positions of the negative control and of the positive control, with the peak at the position of the positive control increasing with the concentration of the pharmaceutical compound increased from 5 µM to 10 µM, and the peak at the position of the negative control decreasing with increasing concentration of the pharmaceutical compound. In this analysis incubation of PBMC aliquots in cell culture medium with the pharmaceutical compound, negative control or positive control was for 30 min, incubation after subsequent addition of fluorescent dye TMRE was for 10 min, both at 37° C., 5% $CO_2$ atmosphere as cell culture conditions.

EXAMPLE 1: MEASUREMENT OF SUSCEPTIBILITY OF CELL LINES FOR APOPTOSIS

As representatives for isolated PBMC, BM or LN mononuclear cells, the B-ALL cell lines SUP-B15, which expresses BCR-ABL (BCR-ABL-positive), and the BCR-ABL negative REH were used in the analytical process in suspension in cell culture medium RPMI1640. As a positive control for MOMP, FCCP was added to 5 µM to one aliquot, as a negative control an aliquot of the suspended cells was used with addition of the same volume of physiological saline, and ABT-199 was added to 10 nM final concentration. After incubation at 37° C. for 3 h, TMRE was added to a final concentration of 50 nM and the aliquots were incubated for further 15 min at 37° C., in a 5% $CO_2$ atmosphere each time. The measurement results by FACS are shown in FIG. 2. For the aliquots containing ABT-199, the MFI is reduced by approx. 40% in the BCR-ABL positive SUP-B15 cells, but for the BCR-ABL negative REH cells, the MFI essentially remains unaffected by ABT-199 in comparison to the negative control. The positive control FCCP shows a reduction of the MFI by 56 to 75% and a shift of TMRE fluorescence.

FIG. 3 shows the results of the FACS analysis when using BV173 cells in the same process measuring TMRE fluorescence (TMRE) at $10^5$ cells per aliquot, and for comparison the results of propidium iodide (PI) staining of aliquots treated in parallel in order to demonstrate that MOMP as determined by TMRE staining precedes cellular apoptosis and can be used a reliable predictor of compound cytotoxicty. The final concentrations ABT-199 (ABT199) or ABT-737 (ABT737) are indicated in FIG. 3. The analytical process using FACS to determine apoptosis had a duration of approx. 3 h. After addition of ABT-199 and ABT-737 as indicated in the figure cells were incubated at 37° C. for 24 h and PI (10 µg/ml) was added and the aliquots were incubated for further 5 min at room temperature. The measurements results by FACS are shown. The results show that for the same concentrations of the pharmaceutical compound, almost identical proportions of cells with MOMP and apoptotic cells were measured by the different processes.

EXAMPLE 2: MEASUREMENT OF SUSCEPTIBILITY OF PBMC FOR APOPTOSIS

PBMC were isolated by density gradient centrifugation using Biocoll from the heparinized blood sample of a patient diagnosed to have CLL (ABT-199, Venetoclax, is approved for treatment of CLL with 17p-deletion). As a comparison, PBMC from a healthy donor were isolated. PBMC were suspended in RPMI1640 cell culture medium and transferred as aliquots into separate tubes, to which ABT-199 was added to a final concentration of 1 µM and incubated at 37° C. for 3 h in a 5% $CO_2$ atmosphere. Subsequently, TMRE was added to 50 nM and aliquots were further incubated for 30 min, then analysed by FACS according to the invention. As a negative control (mock), physiological saline was added, as a positive control FCCP to 5 µM (FCCP).

FIG. 4A shows the results for PBMC from a CLL patient, FIG. 4B shows the results for the PBMC from healthy blood sample. The results demonstrate that after 3 h incubation, the PBMC from the CLL blood sample, the presence of ABT-199 (ABT) as the pharmaceutical compound resulted in a significant reduction of MFI to 53 compared to MFI of 121 in the negative control (mock), and in the positive control (FCCP), MFI of 60.

FIG. 4B, having the same scale as FIG. 4A, shows that in the PBMC from the healthy donor showed a similar MFI of 242 in ABT-199 treated PBMC (ABT) as in the negative control (mock), MFI of 232, i.e. no significant induction of apoptosis. The positive control (FCCP) showed a significant reduction in MFI to 106. This indicates the susceptibility of the PBMC from the CLL donor to induction of apoptosis by ABT-199, and essentially no susceptibility of the PBMC from the healthy donor to induction of apoptosis by ABT-199.

EXAMPLE 3: MEASUREMENT OF SUSCEPTIBILITY OF PBMC FOR APOPTOSIS

PBMC or BM mononuclear cells were isolated by density gradient centrifugation from blood or bone marrow samples originating from patients who were newly diagnosed as ALL (n=12), from blood or bone marrow samples originating from CML patients in chronic phase (CML-CP, n=7), and from blood samples obtained from healthy volunteers (n=6). In accordance with the analytical process, PBMC or BM cells were incubated in cell culture medium with ABT-199 added to 1 µM for 3 h at 37° C. in a 5% $CO_2$ atmosphere for cell culture conditions, followed by addition of TMRE to 50 nM and incubation for another 30 min, then analysed by FACS for fluorescence by TMRE.

The results are shown in FIG. 5, indicating essentially no induction of apoptosis for the PBMC from healthy donors, a strong induction of apoptosis for the PBMC or BM cells from these ALL samples (ALL), and essentially no induction of apoptosis for the PBMC or BM cells from the CML-CP patients. This shows that these specific ALL patients would respond to treatment with ABT-199, whereas these specific CML-CP patients would not respond to treatment with ABT-199.

When using PBMC isolated from cryopreserved blood or mononuclear cells isolated from bone marrow or lymph node samples, the induction of apoptosis by a pharmaceutical compound could also be shown in comparison to a negative control and a positive control, e.g. using FCCP.

EXAMPLE 4: MEASUREMENT OF COMPOUND-SPECIFIC SUSCEPTIBILITY OF A CELL LINE FOR APOPTOSIS

As a representative for isolated PBMC, BM or LN mononuclear cells, SUP-B15 cells were suspended in cell culture medium and processed in the analytical process of the invention as described in Example 1, adding ABT-199 (binding to BCL2) or WEHI-539 (binding to BCL-XL) as pharmaceutical compound to 1 µM final concentration, followed by incubation under cell culture conditions for 3 h. As a positive control, FCCP was added to one aliquot of the cell suspension to 5 µM final concentration. TMRE fluorescence was measured by FACS after 30 min incubation after addition of TMRE.

For comparison, apoptosis was measured by propidium iodide (PI) staining, the entire process having a duration of 24 h.

The results are shown in FIG. 6. Both the process of the invention and the PI staining determined significant induction of apoptosis for ABT-199 (ABT199) and a significantly lower induction of apoptosis by WEHI-539 (WEHI-539). This demonstrates that the analytical process of the invention can identify the effectiveness of a specific pharmaceutical compound for the PBMC tested and that the result can be obtained in a drastically shorter period of time.

EXAMPLE 5: SELECTING AN EFFECTIVE BH3 MIMETIC FOR AN INDIVIDUAL PATIENT

From a blood sample that was drawn from a patient diagnosed to have mantle-cell lymphoma, PBMC were isolated by density gradient centrifugation and suspended in cell culture medium. No further separation of cells was done but all the PBMC were contained in each aliquot dispensed from the isolated PBMC. To separate aliquots of the suspended cells, the following exemplary pharmaceutical compounds were added to a final concentration of 1 µM of one of the following BH3 mimetics: ABT-199, ABT-737 (binding to BCL2, BCL-XL and BCLw, resp.), A1331852, (binding to BCL-XL), or S63845, (binding to MCL1), or FCCP to 5 µM final concentration (positive control for MOMP), or medium (negative control). For measurement, TMRE was added for measuring mitochondrial membrane potential, and for discriminating CD19+ lymphoma cells from normal CD19– cells, anti-CD19 antibody, APC-labelled, was added.

Measurement was by FACS after 3 h incubation under cell culture conditions subsequent to addition of the compounds to the aliquots of the cells.

The FACS results are shown in FIG. 7. The FACS results shown in FIG. 7 were taken in one measurement for each aliquot. Data in the left hand column (a, d, g, j, m, p) show that live and dead cells can be differentiated by measuring forward scatter (FSC) and side scatter (SSC) and a gating can be drawn for dead cells and for live cells (R1, live cells). This gating was applied to the measurement of the dye of the anti-CD19 antibody (CD19 APC) as shown in the center column (b, e, h, k, n, q) (R2). The measurement results for the viable lymphoma CD19+ cells in relation to MOMP are shown in the right hand column (c, f, i, l, o, r), with TMRE fluorescence indicating MOMP, i.e. lower TMRE fluorescence indicating increased MOMP.

The measurement results show that for each aliquot, the gating for live cells (R1) could be determined from forward scatter and side scatter, and that the application of the gating (R2) for live tumour cells to cells identified as CD19+, and the measurement of TMRE fluorescence for CD19+ cells allows the prediction of the effect of each pharmaceutical compound on the proportion of CD19+ tumour cells. An optical comparison of the non-treated CD19+ cells (c, negative control) to the positive control (f, FCCP) shows that the higher TMRE fluorescence cells in the negative control (c) in the positive control (f) are reduced, i.e. the proportion of lower TMRE fluorescence cells is increased, indicating MOMP caused by FCCP. A comparison of the negative control (c) and positive control (f) to the aliquot treated with ABT-199 (i, ABT-199) and to the aliquot treated with ABT737 (l, ABT-737) shows that these compounds are effective in inducing MOMP in these PBMC. The results for the aliquots treated with A1331852 (o) and with S63845 (r) show a less pronounced effect for these compounds of inducing MOMP as indicated by the smaller proportion of reduced TMRE fluorescence in CD19+ cells.

These measurement results show that for this patient sample in comparison to the negative control, the positive control reduces the proportion of cells without MOMP to 15.6%, and that the BH3 mimetics ABT-199 and ABT-737 have a strong effect by reducing the proportion of cells without MOMP to 9.3, respectively 9.9%. The BH3 mimetic A1331852 has a less pronounced effect by reducing the proportion of cells without MOMP to 29.1%, and the BH3 mimetic S63845 has a much less pronounced effect by reducing the proportion of cells without MOMP to 56.7%.

The measurement results for the mean TMRE fluorescence (MeanFL) for the live CD19+ cells are summarized in the following table:

CD19 Gate

|  | MeanFL | % |
| --- | --- | --- |
| negative control | 698 | 100.0 |
| negative control | 708 | 101.4 |
| negative control | 683 | 97.9 |
| FCCP | 109 | 15.6 |
| 1000 nM ABT-199 | 65 | 9.3 |
| 1000 nM ABT-737 | 69 | 9.9 |
| 1000 nM A1331852 | 203 | 29.1 |
| 1000 nM S63845 | 396 | 56.7 |

EXAMPLE 6: MONITORING EFFICACY OF A PHARMACEUTICAL COMPOUND DURING THERAPY AND SELECTING AN EFFECTIVE BH3 MIMETIC FOR AN INDIVIDUAL PATIENT

As an example for patients, NOD/LtSz-scid IL-2γ null (NSG) mice were transplanted intravenously with $10^6$ human BCR-ABL-positive ALL cells (BV173). Treatment started one week after tumour cell inoculation with Dexamethasone (1 mg/kg), Dasatinib (10 mg/kg) and ABT-199 (20 mg/kg) or with solvent (negative control) by oral gavaging 5 days per week.

Full body luminescence imaging for analysis of tumour progression of exemplary mice is shown in FIG. 8 for representative mice, upper row for the negative control treatment (ctrl), lower row for treatment with ABT-199, Dexamethasone and Dasatinib. The combination therapy ABT-199, Dexamethasone and Dasatinib leads to a rapid tumour reduction to even undetectable levels (week 4) and treatment was stopped at week 6. Since bioluminescent image at week 10 (FIG. 8) showed again tumour proliferation we started treatment immediately, but the mouse rapidly died within 6 weeks after treatment with the combination therapy due to drug resistance (week 16).

The imaging shows that in week 1, the control and the ABT-199, Dexamethasone and Dasatinib treatment have similar distributions of tumour cells, especially in the regions of the hips and thorax, but that in weeks 2 to 4, the control mouse has drastically increasing tumour intensity which is spreading over the entire body, whereas the ABT-199, Dexamethasone and Dasatinib treated mouse shows reduction of the tumour, in week 3 only small tumour remnants in the thorax and much smaller tumour at the hips, and in week 4 no detected tumour. In weeks 10, 14 and 16, the tumour in spite of the previous ABT-199, Dexamethasone, Dasatinib treatment recurred, in week 14 approximately corresponding to tumour spread in week 3 in the control mouse, and in week 16 tumour cells had intensely spread over the entire body.

This shows that in spite of the initial therapeutic effect of the treatment with the BH3 mimetic ABT-199, the tumour could not be eradicated completely but recurred, indicating resistance against this pharmaceutical compound.

Spleen cells were isolated from the control mouse after week 4 and from the ABT-199-, Dexamethasone, Dasatinib treated mouse after about 16 weeks. Isolated spleen cells were kept in cell culture medium and treated for 1 h with ABT-199, added to a final concentration of 10 µM, or for 15 min with FCCP, added to a final concentration of 5 µM. Cells were concurrently immunologically stained with APC-labelled anti-human CD45 antibody, to discriminate human leukemic from murine cells, and with TMRE. Measurement was by FACS, with gating for live human cells.

The results are summarized in FIG. 9, showing the TMRE fluorescence of the human CD45+ cells at the beginning of the analytical process (TMRE), set to 100%, with addition of FCCP as positive control, and with addition of ABT-199, relative to the 100%, for the following cells: in vitro cultivated BV173 cells (ctrl (in vitro), black left column each), cultivated spleen cells from the control mouse (ctrl (in vivo), white middle column each), and cultivated spleen cells from one of the ABT-199/DEX/DAS mice (ABT199ABT-199/DEX/DAS, hatched right column each). The CD45+ human cells from the sample originating from the mouse treated with ABT-199, Dexamethasone, Dasatinib showed no response to exposure to ABT-199 in the in vitro analytical process, i.e. the same TMRE fluorescence, indicating no effect of ABT-199 on these cells. The human CD45+ cells originating from the untreated control mouse and the in vitro cultured BV173 cells responded to exposure to ABT-199 by a reduction in TMRE fluorescence to approx. 60%, indicating MOMP in 40% of these cells. The positive control of adding FCCP to these cells resulted in a drastic decrease by approximately 80% to 20% in TMRE fluorescence, indicating strong MOMP in all these cells. This shows that the analytical process can measure a resistance of tumour cells, exemplified here by BV173, against one pharmaceutical compound, wherein the resistance seems to have occurred during the in vivo treatment as shown in FIG. 8 by the reduction of tumour burden until week 4 upon administration of the BH3 mimetic and later recurrence of the tumour.

Cells isolated from the mouse treated with ABT-199/DEX/DAS and cells isolated from the control mouse were subjected to the analytical process using the BH3 mimetics ABT-737, A1331852 and S63845 in separate aliquots. One of these BH3 mimetics was added to a separate aliquot of the cells suspended in cell culture medium to a final concentration of 1 µM. Concurrently, the cells were immunologically stained by adding a APC-labelled anti-human CD45 antibody to identify the tumour cells, and by adding TMRE. After 1 h, cells were analysed by FACS, with the gating set according to side scatter and forward scatter to select for live cells, and to select for CD45+ cells showing TMRE fluorescence.

The result is summarized in FIG. 10, wherein the human CD45+ cells, herein tumour cells, isolated from the control mouse (ctrl (in vivo), white columns), and the cells isolated from the ABT-199/DEX/DAS treated mouse (ABT199/DEX/DAS, hatched columns) show high TMRE fluorescence when exposed to S63845, reduced TMRE fluorescence, i.e. MOMP, when exposed to ABT-737, and strongly reduced TMRE fluorescence, i.e. strong MOMP, when exposed to A1331852.

This shows that the analytical process when carried out on a sample taken at a later point in time from the same patient as a previous sample is suitable to identify a resistance of the tumour cells against one pharmaceutical compound and also to identify the pharmaceutical compounds that have efficacy against the tumour cells.

The invention claimed is:

1. An analytical process for analyzing at least one pharmaceutical compound, comprising:
   (i) isolating mononuclear cells from a blood sample including all (PBMC), bone marrow sample (BM) or lymph node (LN) cells of the sample,
   (ii) transferring the isolated PBMC, BM or LN mononuclear cells into a medium sustaining viability of the PBMC, BM or LN mononuclear cells,
   (iii) adding the at least one pharmaceutical compound to result in at least one concentration of the pharmaceutical compound within separate aliquots of the medium containing the PBMC, BM or LN mononuclear cells, incubating the PBMC, BM or LN mononuclear cells in the medium with the added pharmaceutical compound under cell culture conditions,
   (iv) adding a fluorescent dye labelling active mitochondria in living cells to the separate aliquots of the medium containing the PBMC, BM or LN mononuclear cells and the at least one pharmaceutical compound, and
   (v) measuring on the PBMC, BM or LN mononuclear cells the transmembrane potential of mitochondria by quantification of fluorescence emitted from the dye, wherein the quantification of fluorescence is by fluorescence assisted cell sorting with a gating for live cells determined from forward scatter and side scatter, and wherein the gating for live cells identifies live tumour cells using immunological staining and also identifies live tumour cells as the proportion of cells showing mitochondrial outer membrane permeabilization by quantifying the fluorescence from the dye for measuring the transmembrane potential of mitochondria, both for tumour cells and for non-tumour cells.

2. The analytical process according to claim 1, wherein the at least one pharmaceutical compound is a BH3 mimetic.

3. The analytical process according to claim 1, wherein a combination of at least two pharmaceutical compounds is added to a separate aliquot of the medium containing the PBMC, BM or LN mononuclear cells.

4. The analytical process according to claim 1, wherein the pharmaceutical compound is added to a concentration that is by a factor of at least 2 higher than the pharmacological concentrations adjusted in the patient.

5. The analytical process according to claim 1, comprising adding the pharmaceutical compound to at least two concentrations differing by a factor of at least 10 into different aliquots of the isolated PBMC, BM or LN mononuclear cells, incubating an aliquot of the isolated PBMC, BM, or LN mononuclear cells without addition of the pharmaceutical compound, and after measuring the transmembrane potential of mitochondria by quantification of fluorescence for each aliquot, comparing the fluorescence measurement results.

6. The analytical process according to claim 1, comprising adding to an aliquot of isolated PBMC, BM or LN mononuclear cells a cell-permeable protonophor, incubating the aliquot containing the protonophor, and after measuring the transmembrane potential of mitochondria by quantification of fluorescence for each aliquot, comparing the fluorescence measurement results.

7. The analytical process according to claim 1, comprising isolating the mononuclear cells from a blood, bone marrow or lymph node sample by density gradient centrifugation, lysis of erythrocytes and resuspending the isolated mononuclear PBMC, BM or LN cells in the medium sustaining viability of PBMC, BM, or LN mononuclear cells.

8. The analytical process according to claim 1, wherein the blood, bone marrow or lymph node sample originates from a patient for whom no diagnostic procedure for leukemia or lymphoma has been finished.

9. The analytical process according to claim 1, wherein the blood, bone marrow or lymph node sample originates from a patient diagnosed as having a relapse of leukemia or lymphoma.

10. The analytical process according to claim 1, wherein at least two different pharmaceutical compounds are added to separate aliquots of the isolated PBMC, BM cells or LN mononuclear cells and are processed under the same conditions.

11. The analytical process according to claim 1, wherein the process is finished in no more than 3 hours as measured from the end of the isolation of mononuclear cells from the blood, bone marrow or lymph node sample.

12. The analytical process according to claim 1, wherein subsequent to the process being carried out on an initial sample, the process is additionally carried out on at least one sample, which originates from the same patient at a later point in time, wherein to an aliquot of isolated PBMC, BM or LN mononuclear cells in the medium the same at least one pharmaceutical compound is added as that for which the process was carried out on an initial sample, for monitoring the efficacy of the at least one pharmaceutical compound on the sample originating from the same patient at a later point in time.

13. The analytical process according to claim 1, wherein subsequent to the process being carried out on an initial sample, the process is additionally carried out on at least one sample, which originates from the same patient at a later point in time, wherein at least two pharmaceutical compounds are added to a separate aliquot in each case, for monitoring the efficacy of at least two different pharmaceutical compounds and/or for the determination of the pharmaceutical compound which has the more intense efficacy against the leukemia or lymphoma cells.

14. The analytical process according to claim 1, wherein for the same aliquot quantification of fluorescence by FACS is made for non-tumour cells, which in immunological staining are negative for at least one of CD19, CD3, CD4, CD8, CD34, CD33, CD117, or have CD45 high expression.

15. The analytical process according to claim 1, wherein the tumour cells are lymphoma and/or leukemia cells selected from the group consisting of CD19+ cells, CD3+ cells, CD4+ cells, CD8+ cells, CD34+ cells, CD33+ cells, CD45+ low expression cells, or CD117+ cells.

16. The analytical process according to claim 1, using the process for selecting from the at least two pharmaceutical compounds the pharmaceutical compound that has the higher efficacy for inducing MOMP in tumour cells on the basis of quantification of fluorescence emitted from the dye labelling active mitochondria.

* * * * *